United States Patent [19]  [11] 4,110,372
Hey et al.  [45] Aug. 29, 1978

[54] PROCESS FOR THE PURIFICATION OF CARBOXYLIC ACIDS

[75] Inventors: Hansjörg Hey, Hofheim, Taunus; Helmut Schaum, Bad Soden am Taunus; Hans-Jürgen Arpe, Fischbach, Taunus, all of Fed. Rep. of Germany

[73] Assignee: Hoechst Aktiengesellschaft, Frankfurt am Main, Fed. Rep. of Germany

[21] Appl. No.: 603,940

[22] Filed: Aug. 12, 1975

Related U.S. Application Data

[63] Continuation-in-part of Ser. No. 419,291, Nov. 27, 1973, abandoned.

[30] Foreign Application Priority Data

Nov. 29, 1972 [DE] Fed. Rep. of Germany ....... 2258441

[51] Int. Cl.² ............................................. C07C 51/42

[52] U.S. Cl. .................................... 260/540; 260/408; 260/419; 260/514 R; 260/514 J; 260/514 K; 260/525; 260/526 N; 260/535 R; 260/537 R; 260/538; 260/539 A; 260/541

[58] Field of Search .................. 260/540, 541, 515 R, 260/526 N, 537 R, 419, 538, 539 A, 514 R

[56] References Cited

U.S. PATENT DOCUMENTS 2,770,585  11/1956  Smith et al. ......................... 260/541

FOREIGN PATENT DOCUMENTS 807,987  5/1974  Belgium .................................. 260/515

*Primary Examiner*—Vivian Garner
*Attorney, Agent, or Firm*—Curtis, Morris & Safford

[57] ABSTRACT

A process for the removal of formic acid from a crude mixture thereof with carboxylic acids by reacting the formic acid component of the mixture with a carboxylic anhydride and/or a compound forming an anhydride with a carboxylic acid, which comprises carrying out the reaction in the presence of an acidic catalyst.

11 Claims, No Drawings

PROCESS FOR THE PURIFICATION OF CARBOXYLIC ACIDS

This is a continuation-in-part of application Ser. No. 419,291 filed Nov. 27, 1973, now abandoned.

The present invention relates to an improved process for the purification of carboxylic acids containing formic acid.

Different chemical processes for oxidative manufacture of carboxylic acids yield a crude product contaminated with formic acid. Because of the presence of formic acid in relatively high concentrations as a consequence of certain processes, a direct use of these carboxylic acids or their processing is often impossible. Industrial grade acetic acid, for example, generally should contain no more than 0.03% of formic acid. The crude acid obtained in various processes for oxidative manufacture of acetic acid, however, contains more than 0.2% of formic acid. In such cases, therefore, the formic acid must be removed.

Various processes are known to reduce the content of formic acid in carboxylic acids important for large-scale manufacture, for example acetic acid. Thus, the formic acid may for example be removed from the crude acid during the distillation work-up or also be decomposition on catalysts.

The distillation purification of crude carboxylic acids, especially acetic acid, requires great technical expenditure in order to reduce the content of formic acid to the desired residual concentration. Because of the strongly corrosive properties of hot formic acid, this distillation requires also the use of expensive resistant materials. Furthermore, the corrosive effect increases disproportionately with increasing concentration of formic acid. Therefore, such parts of the column are especially affected where a high concentration of formic acid necessarily occurs in order to keep down losses of a carboxylic acid to be purified.

A decomposition of the formic acid contained in the crude acid is possible above all by means of catalysts containing metals, especially metals of the 8th group of the Periodic System or compounds thereof. The formic acid may in principle be removed by means of homogeneous catalysts of this kind in the liquid phase, but for reasons of industrial requirements, the removal is generally carried out in the vapor phase at high temperatures using carrier catalysts. The platinum metal-containing catalysts usually employed require a series of expensive precautions in order to prolong the life of a catalyst as long as possible for reasons of cost. Thus, in some processes, a pretreatment of the crude acid with an absorbing material before the decomposition of the formic acid is necessary to remove substances which cause a rapid poisoning of the catalyst. In other processes where, for example, acidic copper, iron, cobalt or nickel salts are used as catalysts, it is necessary to pass a large amount of air or other oxidation agents over the catalyst together with the vapors of the crude acid, because otherwise the formic acid would not decompose as desired and the life of the catalyst would be too short. When carboxylic acids, especially those having more than 2 carbon atoms, are purified, the catalytic decomposition of the formic acid at high temperatures under oxidation conditions causes simultaneously an oxidation degradation of the carboxylic acid to be purified and thus corresponding losses.

A further known reaction for the decomposition of formic acid is limited to pure formic acid itself, and not directed to a decomposition of the formic acid to effect a purification, but to the manufacture of carbon monoxide by reaction of formic acid with concentrated sulfuric acid. The removal of formic acid being present in carboxylic acid only in small concentrations by this process at a sufficient reaction rate (see Comparative Example 2) is possible only in the presence of a very large amount of concentrated sulfuric acid and thus causes corrosion and disposal problems when applied in industry.

Furthermore, the literature describes processes wherein mixed anhydrides may be obtained from formic acid and carboxylic anhydrides. These anhydrides are employed as intermediate products for further reactions, whereby, in a side reaction, the mixed anhydride may be split to form carbon monoxide and carboxylic acid.

In principle, formic acid may also be removed from carboxylic acid mixtures by addition of carboxylic anhydrides. However, the reaction rate decreases rapidly with decreasing formic acid concentration in the reaction mixture, so that even at long reaction times a complete removal of the formic acid cannot be obtained (see Comparative Example 1). Therefore, anhydride was used in excess, and after the reaction, non-consumed anhydride was converted to acid by adding water. But this operation mode is very expensive. An acceleration of the reaction speed was attained also by adding pyridine, but in this case, the base added had to be removed by a distillation work-up.

The present invention provides an improved process for removing formic acid from a crude mixture thereof with an aliphatic or cycloaliphatic carboxylic acid having 2 to 16 carbon atoms or with an aromatic monocarboxylic acid having 6 to 8 carbon atoms by reacting the formic acid component of the mixture with a carboxylic anhydride, a compound forming an anhydride with a carboxylic acid, or a mixture thereof, which comprises carrying out the reaction at a temperature from about 20° to 300° C in the presence of an acidic catalyst which is a mineral acid, a sulfonic acid, an acidic salt of a mineral acid, or a heterogeneous acidic catalyst selected from the group consisting of acidic ion exchange resins in the $H^+$ form and acid-activated bentonites and zeolites.

The advantage of the process of the invention resides above all in the fact that the removal of formic acid from carboxylic acids by reaction with anhydrides gives especially high space-time yields without requiring a removal of soluble basic catalysts after the reaction.

The removal of formic acid from crude carboxylic acids according to the process of the invention is based on the reaction of formic acid with carboxylic anhydrides to yield carboxylic acids corresponding to the anhydrides and carbon monoxide. The structure, and number of carbon atoms of the carboxylic acid to be purified is, therefore, not critical for the reaction on which the invention is based.

The process according to the invention is suitable for the purification of aliphatic monocarboxylic acids containing formic acid and having from 2 to 16 carbon atoms, preferably from 2 to 8 carbon atoms, such as, for example, acetic acid, propionic acid, butyric acid, valeric acid, or caproic acid. The aliphatic carboxylic acids may be linear or branched or may have a cycloaliphatic carbon skeleton, for example as cyclohexane carboxylic acid. They may be unsaturated, such as acrylic acid or crotonic acid and may contain inert substituents in their hydrocarbon radicals, such as alkoxy groups, ester groups, or halogen atoms, as in the case of chloroacetic acid, without the reaction between formic acid and the carboxylic anhydride being hindered. Aliphatic di- and poly-carboxylic acids having from 2 to 16 carbon atoms, preferably oxalic acid, malonic acid and acids derived therefrom, as well as dicarboxylic acids having from 5 to 8 carbon atoms the carboxyl groups of which are separated from each other by more than 2 carbon atoms, for example adipic acid or pimelic acid. Also aromatic carboxylic acids having from 7 to 16 carbon atoms, preferably aromatic monocarboxylic acids having 7 or 8 carbon atoms, such as benzoic acid or toluenecarboxylic acid can also be purified by the process of the invention.

The crude acid from which formic acid is removed may contain inert impurities, foreign constituents or solvents, as far as they are inert to the carboxylic anhydrides, for example low boiling aliphatic or aromatic hydrocarbons or halohydrocarbons, ethers and esters. The main proportion of reactive impurities such as water or alcohols should be removed prior to the treatment according to the invention. In the case of water being present in the crude product simply an excess of carboxylic anhydride necessary for the decomposition of the water is used.

As compared to other processes, the removal of formic acid according to the invention is an especially gentle and selective process.

Generally, an equimolar amount of the anhydride relative to formic acid is used, but the reaction is also possible when an excess of anhydride is employed. Even in the case of a deficiency of anhydride, the reaction speed of the process of the invention is not decreased.

The concentration of formic acid in the crude carboxylic acid to be purified may vary within wide limits. Thus, for example, formic acid being present in the crude acid in a concentration of less than 0.03% may be decomposed according to the process of the invention, but this decomposition is also possible when the concentration of formic acid is substantially greater.

In principle, the anhydrides of aliphatic and/or aromatic monocarboxylic acids may be used for removing the formic acid according to the process of the invention. There are no special purification requirements for these anhydrides. Also compounds from which the carboxylic anhydrides are formed by reaction with carboxylic acids, for example ketene or carboxylic acid halides, or mixtures of these compounds with carboxylic anhydrides may be employed for the process of the invention. For removing the formic acid, there are preferably used such compounds and/or carboxylic anhydrides from which, in the reaction with formic acid, only that carboxylic acid is formed which is already present as crude acid. Therefore, in order to remove formic acid from industrial grade acetic acid, acetic anhydride is preferably employed.

As acidic catalyst, mineral acids, for example hydrochloric or sulfuric acid, or sulfonic acids such as p-toluenesulfonic acid, or acidic salts may be added to the crude acid mixture.

An acidic salt, often referred to as "acid salt," is a salt in which not all the replaceable hydrogen atoms of the respective acid have been replaced by a radical or an element. Salts of this type yield hydrogen ions and react like acids, for example $NaHSO_4$, $Na_2HPO_4$, or $NH_4H_2PO_4$.

Especially appropriate are heterogeneous acidic catalysts such as acidic ion exchangers or activated bentonites or zeolites, for example activated montmorillonites or activated bleaching earths which have been treated in the cold with a mineral acid, for example hydrochloric or sulfuric acid. After complete reaction, these catalysts insoluble in the crude carboxylic acid may be separated from the reaction mixture in a very simple manner by filtration or centrifugation. They are therefore especially suitable for a large-scale manufacture.

For a discontinuous operation, the catalysts generally are added to the reaction mixture in amounts of from 0.01 to 10%, preferably from 0.1 to 2%, relative to the weight of the crude carboxylic acids.

When the catalyst is insoluble in the reaction mixture because of a high molecular weight or polymer structure, the processes usual in the case of employing such catalyst systems, for example operating in the sump or trickling phase, may be applied. A catalyst of polymer structure may be arranged in a solid or fluidized bed. In these continuous processes, even at small catalyst amounts high space-time yields may be attained.

The decomposition of formic acid with carboxylic acid anhydrides may be carried out in the liquid or in the gaseous phase.

The process of the invention is generally carried out at a reaction temperature of from 20° C. to 300° C., preferably from 100° C. to 200° C.

The formic acid may be decomposed at normal, reduced or elevated pressure, the decomposition generally being carried out at a pressure of from 1 to 3 atmospheres.

The following examples illustrate the invention.

COMPARATIVE EXAMPLE 1

In a glass flask provided with dropping funnel, reflux condenser and bubble counter, and connected to a gas buret, 500 g of industrial grade acetic acid containing 0.04% of water and 0.6% of formic acid (according to titration with lead tetra-acetate) was heated to boiling temperature, and subsequently 8.5 g of acetic anhydride were added.

At a reaction temperature of 118° C. and at decreasing speed, a total of 1340 ml of carbon monoxide developed within 300 minutes. After this time, the industrial grade acetic acid contained still 0.1% of formic acid, that is, 83% of formic acid were decomposed.

COMPARATIVE EXAMPLE 2

To 200 g of the industrial grade acetic acid described in Example 1, 0.2 ml of concentrated sulfuric acid were added and the whole was heated to 118° C. for 220 minutes. After this time, 0.4% of formic acid was still detected in the reaction solution.

EXAMPLE 1

200 g of the industrial grade acetic acid described in Example 1 were heated to 118° C., and subsequently, 0.2 ml of concentrated sulfuric acid and 3.3 g of acetic anhydride were added. The gas formation in this test was substantially more rapid than in Comparative Example 1. After a reaction time of 45 minutes, the content of formic acid in the industrial grade acetic acid was only 0.002%, that is, 99.7% of the formic acid was removed.

EXAMPLE 2

As acidic heterogeneous catalyst, a macroreticular polystyrene-divinylbenzene resin having sulfonic acid groups in the $H^+$ form, a pore diameter of from 200 to 1300 Å, a specific surface of 60 m² per gram and a grain size of from 0.3 to 1.2 mm was used. The maximum capacity of the exchanger resin was 2.9 equivalents/liter. For a continuous reaction, a horizontally arranged reaction tube with a jacket, having a length of 260 mm and a diameter of 30 mm, and heated to 115° C. was used. The tube was divided by means of porous sintered glass plates into 4 chambers each having a capacity of 45 ml. The chambers, from each of which a gas outlet tube projected vertically, were charged with a total of 90 g of the ion exchanger described above.

For removing the formic acid, 23.2 g of acetic anhydride were added to 3150 g of industrial grade acetic acid containing 0.2% of formic acid and 0.04% of water. From this reaction solution, 1500 g per hour were pumped through the reaction tube after having passed through a preheating zone also heated to 115° C. 3169 g of acetic acid were obtained containing 0.004% of formic acid, that is, 98% of the formic acid had been converted.

EXAMPLE 3

572 g of acetic anhydride were added to 3174 g of industrial grade acetic acid which, as a crude product of the distillation work-up of an acetic acid manufacturing plant, contained 5.8% of formic acid and 0.8% of water. From this reaction solution, 2700 g per hour were pumped through the apparatus heated to 115° C. as described in Example 2. 3630 g of acetic acid having a formic acid content of 0.003% were obtained, that is, more than 99.9% of the formic acid had been converted.

EXAMPLE 4

200 g of propionic acid having a formic acid content of 0.5% were heated to 140° C., and 4 g of propionic anhydride and 0.2 ml of concentrated sulfuric acid as catalyst were added. After a reaction time of 105 minutes, the propionic acid contained 0.002% of formic acid; that is, 99.6% of the formic acid had been converted.

EXAMPLE 5

37 g benzoic anhydride and 0.4 g sulfuric acid were added to a solution of 20 grams benzoic acid in 60 g acetic acid and 3.33 g (72.4 millimoles) formic acid. At 100° C., 72.1 millimoles carbon monoxide developed within 30 minutes and the formic acid was decomposed practically completely.

EXAMPLES 6 TO 9

14.8 g acetic anhydride were added at 100° C. to mixtures of 92 g acetic acid, 20 g of a carboxylic acid as defined in the following table and 3.33 g (2.89% by weight) formic acid and 1.0 g of the sulfonic acid ion exchanger described in Example 2. The experiments were interrupted when the initially vigorous development of CO had substantially subsided and the reaction solutions were analyzed as to their content of formic acid. The results are listed in the following table.

| Example | carboxylic acid in addition to acetic acid | reaction time (minutes) | residual HCOOH after reaction |
|---|---|---|---|
| 6 | benzoic acid | 35 | 0.015 % |
| 7 | monochloroacetic acid | 40 | 0.01 % |
| 8 | stearic acid | 35 | 0.01 % |
| 9 | adipic acid | 50 | 0.25 % |

EXAMPLE 10

In the manner described in Examples 6 to 9 a mixture of 112 g acetic acid and 3.33 g (2.89% by weight) formic acid was reacted with acetic anhydride. After a reaction time of 35 minutes the residual formic acid content was found to be 0.03%.

EXAMPLE 11

1 g of the sulfonic acid ion exchanger described in Example 2 and 14.8 g acetic anhydride were added to a mixture of 112 g caproic acid and 3.33 g (2.89% by weight) formic acid and the whole was heated for 50 minutes to 100° C. After this time, the reaction solution only contained 0.025% formic acid.

EXAMPLE 12

0.4 g sulfuric acid and 14.8 g acetic anhydride were added to a mixture of 30 g cyclohexane carboxylic acid and 3.33 g (10% by weight) formic acid and the whole was heated for 10 minutes to 100° C. After the treatment, the reaction solution only contained 0.01% formic acid.

EXAMPLES 13 TO 15

14.8 g acetic anhydride and an acidic salt as defined in the following table as catalyst were added at 100° C. to a mixture of 112 g acetic acid and 3.33 g (2.89% by weight) formic acid. When the development of CO had ceased, the residual content of formic acid in the reaction solution was analyzed. The result is likewise indicated in the following table.

| Example | acidic salt as catalyst type | (g) | amount (mmoles) | reaction time (minutes) | residual HCOOH after reaction % |
|---|---|---|---|---|---|
| 13 | $NaHSO_4 \cdot H_2O$ | 1.13 | 8.2 | 60 | 0.005 |
| 14 | $(NH_4)H_2PO_4$ | 0.46 | 4.0 | 190 | 0.04 |
| 15 | $(NH_4)_2HPO_4$ | 1.08 | 8.2 | 130 | 0.05 |

We claim:

1. In a process for removing formic acid from a crude mixture thereof with a carboxylic acid selected from the group consisting of lower fatty acids other than formic acid by reacting the formic acid component of the mixture with a carboxylic anhydride, a compound forming an anhydride with a carboxylic acid, or a mixture thereof, the improvement which comprises carrying out the reaction at a temperature of from about 20° C. to 300° C. in the presence of an acid catalyst which is a mineral acid, a sulfonic acid, an acidic salt of a mineral acid or a heterogeneous acid catalyst selected from the group consisting of acidic ion exchange resins in the $H^+$ form and acid-activated bentonites and zeolites.

2. The process defined in claim 1 in which the acid catalyst is sulfuric acid.

3. The process defined in claim 1 in which the reaction is carried out at a temperature of from 100° C. to 200° C.

4. The process as defined in claim 1 in which the acidic catalyst is an acidic salt of a mineral acid.

5. The process as defined in claim 1 in which acetic acid containing formic acid as an impurity is reacted with acetic anhydride.

6. The process defined in claim 1 in which the acid catalyst is an acidic ion exchange resin in the H+ form.

7. The process defined in claim 6 in which the acid catalyst is a macroreticular polystyrene-divinylbenzene resin having sulfonic acid groups in the H+ form.

8. The process as defined in claim 1, wherein said lower fatty acid is acetic acid.

9. The process defined in claim 8 in which acetic acid containing formic acid as an impurity is reacted with acetic anhydride, ketene or a mixture thereof.

10. The process as defined in claim 1, wherein said lower fatty acid is propionic acid.

11. The process defined in claim 1 in which propionic acid containing formic acid as an impurity is reacted with propionic acid anhydride.

* * * * *